US006455585B1

United States Patent
Del Castillo Nieto et al.

(10) Patent No.: US 6,455,585 B1
(45) Date of Patent: Sep. 24, 2002

(54) ESTERS DERIVED FROM SUBSTITUTED PHENNYL-CYCLOHEXYL COMPOUNDS

(75) Inventors: Juan Carlos Del Castillo Nieto, Barcelona; Joan Huguet Clotet, Sant Joan Despi; Elisabet De Ramon Amat, Barcelona; Maria Chalaux Freixa, Barcelona; Marisabel Mourelle Mancini, Barcelona, all of (ES)

(73) Assignee: Vita Invest, S.A., Sant Joan Despi (ES)

( * ) Notice: Subject to any disclaimer, the term of this patent is extended or adjusted under 35 U.S.C. 154(b) by 0 days.

(21) Appl. No.: 09/831,177

(22) PCT Filed: Nov. 4, 1999

(86) PCT No.: PCT/ES99/00352

§ 371 (c)(1),
(2), (4) Date: May 4, 2001

(87) PCT Pub. No.: WO00/27799

PCT Pub. Date: May 18, 2000

(30) Foreign Application Priority Data

Nov. 6, 1998 (ES) .................................................. 9802329

(51) Int. Cl.$^7$ .......................... C07C 69/78; C07C 69/88; A61K 31/235; A61P 25/04
(52) U.S. Cl. ........................... 514/533; 560/32; 560/37; 560/56; 560/57; 560/105; 514/544
(58) Field of Search ............................. 560/32, 37, 56, 560/67, 105; 514/506, 646

(56) References Cited

U.S. PATENT DOCUMENTS

| | | | | |
|---|---|---|---|---|
| 3,652,589 A | * | 3/1972 | Flick et al. ............... | 260/326.5 |
| 5,733,936 A | * | 3/1998 | Buschmann et al. ......... | 514/646 |
| 5,811,582 A | * | 9/1998 | Buschmann et al. ........ | 514/646 |

* cited by examiner

*Primary Examiner*—Robert W. Ramsuer
*Assistant Examiner*—Golam M. M. Shameem
(74) *Attorney, Agent, or Firm*—Steinberg & Raskin, P.C.

(57) ABSTRACT

New esters derived from substituted phenyl-cyclohexyl compounds, which are derived from Tramadol, process for obtaining them and their use for preparing a drug with analgesic properties. These new compounds of general formula (I) have a higher analgesic activity, a lower toxicity and a longer effective time period than Tramadol.

11 Claims, No Drawings

ESTERS DERIVED FROM SUBSTITUTED PHENNYL-CYCLOHEXYL COMPOUNDS

This application is a 371 of PCT/ES99/00352 filed Nov. 04, 1999.

FIELD OF THE INVENTION

The present invention relates to new esters derived from substituted phenyl-cyclohexyl compounds, which are derived from Tramadol. The obtained compounds have a higher analgesic activity, a lower toxicity and a longer effective time period than Tramadol.

BACKGROUND OF THE INVENTION

The treatment of pain is of great importance in the field of medicine. The pharmacological agents presently used for the treatment of pain can be primarily classified into two large groups: opioid compounds and non-steroidal anti-inflammatories (NSAIs). The NSAIs are only useful in the case of light or moderate pain; severe pain has traditionally been treated with opiod compounds. However, these opioid compounds have several undesirable side effects, such as constipation, respiratory depression, tolerance and possibility of addiction.

U.S. Pat. No. 3,652,589 describes a type of analgesic compounds with a structure of substituted cycloalkanol phenol ethers having a basic amino group in the cycloalkyl ring. Among them the (1R, 2R or 1S, 2S)-2-[(dimethylamino)methyl]-1-(3-methoxyphenyl) cyclohexanol compound, generally known as Tramadol, is specially noted and specifically claimed in said patent.

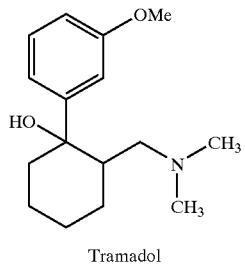

Tramadol

A series of products derived from the above, in which the dehydration in the cycloalkanol ring has occurred together with the demethylation of the methoxyl in the 3 position of the phenyl ring, of structure:

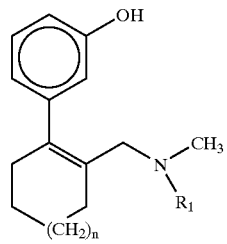

have been described in the Dutch patent NL 6610022.

This patent also describes products derived from those of said US patent, in which the methoxyl group in the 3 position of the phenyl ring has been demethylated. That is, products of structure:

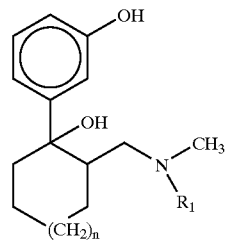

O-demethyltramadol is included among those products described in patent NL 6610022, said product having been described as one of the metabolization products of Tramadol (Von W. Lintz et al. Arzneim-Forsch (*Drug Res*) 31 (II); 1932–43 (1982). The analgesic activity of Tramadol is attributed to its (+) isomer (Lars Poulsen et al. *Clin. Pharmacol. Ther* (St. Louis) 1996, 60 (6), 636–644). However, there is no data as to the clinical use of the O-demethyltramadol metabolite.

More recently, in patent EP 753506, new derivatives of Tramadol have been described, which are O-demethylsubstituted, halogenated at position 1 and/or 3-cyclohexyl substituted.

Tramadol has an opioid agonist effect. However, the clinical experience with Tramadol shows that in spite of this, it does not present some of the side effects typical of the opioid agonists, such as respiratory depression (W. Vogel et al. *Arzneim. Forsch* (*Drug Res*) 28 (I), 183 (1978)), constipation (I. Arend et al. *Arzneim. Forsch* (*Drug Res*) 28 (I), 199 (1978), tolerance (L. Flohe et al., *Arzneim. Forsch* (*Drug Res*) 28 (I), 213 (1978)) and possibility of abuse (T. Yenagita et al., *Arzneim. Forsch* (*Drug Res*) 28 (I), 158 (1978)). Some side effects specific for Tramadol have been found, which are caused when it is injected intravenously (i.v.) and quickly, such as hot flushes and sweating.

Another of the disadvantages associated with Tramadol is its short effective time period (T. Matthiesen, T. Wohrmann, T. P. Coogan, H. Uragg, "The experimental toxicology of tramadol: an overview", *Toxicology Letters* 95, 63–71, (1998)).

U.S. Pat. No. 5,733,936 (hereinafter, "the '936 patent) discloses some esters of 6-dimethylaminomethyl-1-phenyl-cyclohexane in the general formula of the description section with analgesic activity and low toxicity.

The object of the '936 patent is to obtain esters, phosphates, ethers, phenols, carbonates, carbamates, etc of derivatives of 6-dimethylaminomethyl-1phenyl-cyclohexane, said derivatives can be substituted in the 5-position of ciclohexyl (according to the meaning of $R^2$ and $R^3$ of the claims) as well as of tehir dehydroxilated, chlorinated, phluorated analog compounds.

Moreover, although the '936 patent discloses some esters of 6-dimethylaminomethyl-1-phenyl-cyclohexane, none of the examples in the '936 patent refer to the ester of O-demethyltramadol. None of these examples includes compounds which have the tertiary OH characteristic of O-demethyltramadol. In particular, Example 13 which is the closest to the application discloses an ester of an analog of O-demethyltramadol with acetyl salicylic acid and not an ester of O-demethyltramadol. Therefore, the '936 patent does not disclose an ester of O-demethyltramadol with the characteristic hydroxyl group in the 1-position. The '936 patent discloses no working examples of an ester of O-demethyltramadol. The three other esters examplified (Examples 14, 15, 16) also lack the tertiary hydroxyl group.

Therefore, stability, activity and side effects data could not have been foreseen nor suggested. According to the present application a surprising effect is achieved with the compounds of formula I.

Based on the above background of the invention, the compounds with an analgesic activity similar to or higher than that of Tramadol and with a lower toxicity and with a higher effective time period are still of interest.

DESCRIPTION OF THE INVENTION

The present invention relates to new esters of O-demethyltramadol or its 1,2-dehydrated derivative.

The analgesic activity of these compounds has been found to be higher than that of Tramadol with a lower toxicity and a longer effective time period when administered orally (see FIG. 1).

In particular, the present invention describes and claims those products of general formula (I), its salts and optical isomers, as well as the process for obtaining them.

The products of the present invention are represented by the following general formula (I):

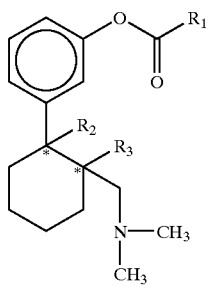

Shows possibility of asynumetric carbons where $R_1$ is:

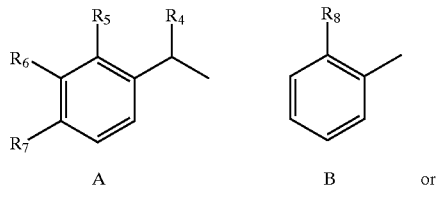

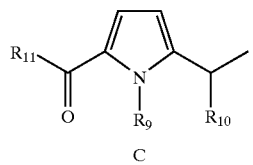

$R_2$ is: OH;
$R_3$ is: H;
or $R_2$ and $R_3$ together form a double bond;
$R_4$ is: H or $C_1$–$C_2$ alkyl;
$R_5$ is: H, $NH_2$, NH—$R_{11}$ or O—$R_{11}$;
$R_6$ is: H, CO—$R_{11}$, O—$R_{11}$ or halogen;
$R_7$ is: H, $C_1$–$C_5$ alkyl, $C_2$–$C_5$ O-alkenyl, phenyl, or $R_6$ and $R_7$ are —Ch=$CR_{12}$–$CR_{13}$=CH—, forming an optionally substituted condensed aromatic ring;
$R_8$ is: OH, —O—CO—N $(CH_3)_2$ or NH—$R_{11}$;
$R_9$ and $R_{10}$ are: H or $C_1$–$C_4$ alkyl, whether equal ordifferent, or form a —$CH_2$—$CH_2$— group;

$R_{11}$ is: phenyl; phenyl optionally substituted by 1 or more of the following substituents: halogen (Cl, Br, I), $NO_2$, $C_1$–$C_6$ alkyl, $C_2$–$C_6$ alkenyl, OH, or $NH_2$;

$R_{12}$ and $R_{13}$ are: H, or $C_1$–$C_3$ O-alkyl, whether equal or different.

When $R_1$ is A, preferably, $R_4$ is methyl or H, $R_5$ is $NH_2$, 2,5-dichlorophenylamino or H, $R_6$ is substituted CO-phenyl or H, $R_7$ is isobutyl or H, or $R_6$ and $R_7$ form a substituted condensed aromatic ring.

More preferably, when $R_1$ is A, the products are:

3-(2-dimethylaminomethyl-1-hydroxy-cyclohexyl)-phenyl 2-(4-isobutyl-phenyl)-propionate 3-(2-dimethylaminomethyl-1-hydroxy-cyclohexyl) phenyl 2-(6-methoxy-naphthalen-2-yl)-propionate 3-(2-dimethylaminomethyl-cyclohex-1-enyl)-phenyl 2-(4-isobutyl-phenyl)-propionate 3-(2-dimethylaminomethyl-cyclohex-1-enyl)-phenyl 2-(6-methoxy-naphthalen-2-yl)-propionate When $R^1$ is B, preferably, $R_8$ is OH or —O—CO—N $(CH_3)_2$.

More preferably, when $R_1$ is B, the products are:

3-(2-dimethylaminomethyl-1-hydroxy-cyclohexyl)-phenyl 2-hydroxybenzoate 3-(2-dimethylaminomethyl-cyclohex-1-enyl)-phenyl 2-hydroxybenzoate 3-(2-dimethylaminomethyl-1-hydroxy-cyclohexyl)-phenyl 2-dimethylcarbamoyloxy-benzoate 3-(2-dimethylaminomethyl-cyclohex-1-enyl)-phenyl 2-dimethylcarbamoyloxy-benzoate.

When $R_1$ is C, preferably, $R_9$ is methyl or H or forms a —$CH_2$—$CH_2$— group with $R_{10}$. More preferably, when $R_1$ is C, the products are:

3-(2-dimethylaminomethyl-1-hydroxy-cyclohexyl) phenyl 5-benzoyl-2,3-dihydro-1H-pyrrolizine-1-carboxylate.

DESCRIPTION OF THE METHODS

The compounds of general formula (I) of the present invention can be obtained by a general process which is characterised by reacting a compound of general formula (II) with the corresponding acid or acid derivative of general formula III.

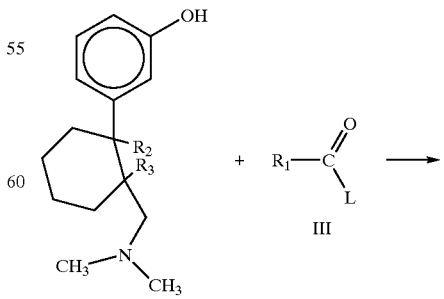

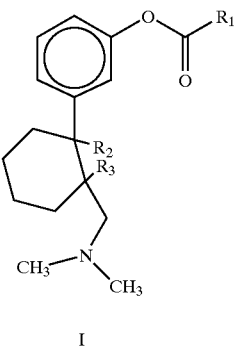

Where $R_1$, $R_2$, $R_3$ have the above defined meaning, and L=OH, halogen,

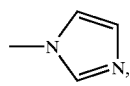

O—$R_{14}$ or —CO—$R_{15}$,
being
  $R_{14}$=$C_{1-6}$ alkyl, phenyl, optionally substituted phenyl, and
  $R_{15}$=alkyl, a phenyl ring optionally substituted by one or more substituents or a heterocyclic ring optionally substituted by one or more substituents.
Preferably L is OH or Halogen.

The reaction is carried out in an inert solvent, preferably dichloromethane, tetrahydrofuran, etc., in a temperature range of −20° to 120° C., preferably a range of 0° to 35° C., and preferably in the presence of a condensation promoting agent, such as carbonyldiimidazol, dicyclohexylcarbodiimida, etc.

The compounds of formula (II) are obtained according to the methods disclosed in the literature (NL 6610022 or Flick et al. *Arzneim. Forsch/Drug Res.* (1978), 28 (I), 107–113).

DESCRIPTION OF THE PHARMACOLOGICAL PROCESSES

Analgesic Activity Tests

The pharmacological activity of the products of the present invention was tested in vivo in several experimental models, which are known to evaluate the pain in animals.

a) Hot Plate Method

The method that was used is described by Eddy N. B. and Leimbach D. (J. Pharm. Exp. Ther. 107: 385–393, 1953). The analgesic effect of the products was evaluated analysing the behaviour of the animals on a hot surface at 55° C.±1° C.

Male Swiss mice weighing 20–25 g were used. The compounds being tested were administered orally or intraperitoneally 1 hour o 30 minutes before starting the test, respectively.

The process consisted of placing the animals on the plate and keeping them in a Plexiglas cylinder 25 cm high and 21 cm high. The time the animals took to jump off the hot surface was determined. The animals were selected before starting the test so that those that took longer than 10 seconds to jump off were not included in the group that would receive treatment.

30 minutes after administering the product being tested, the test was repeated and the maximum time it took the animals to jump off was again recorded. Those animals that did not jump off after 60 seconds were removed from the plate to avoid any injuries and were recorded as 100% protection.

The results are expressed as the C of jump time increase calculated as follows:

$$\% \text{ jump time increase} = \frac{(\text{treated jump time} - \text{base jump time})}{\text{base jump tieme}} \times 100$$

In order to determine the duration of the analgesic effect of the orally administered products, the analgesic activity was evaluated on the hot plate 1, 3, 6, 8, and 24 hours after the administration of the product, as well as the control group which received treatment only with the vehicle. The base responses were evaluated at 30 and 5 minutes prior to administering the products.

b) Determination of the DL50 in the Products.

(EUDRA/S/87/011, Single Dose Toxicity, European Directive 75/318/EEC) (ICH S4, Toxicity Studies, single dose and repeated dose, CPMP vol III Feb. 87, Single dose toxicity)

Male Swiss mice of the same batch weighing 20–25 g are used in order to estimate the acute toxicity of the products.

Prior to administering the products, the animals were forced to fast for 12 hours with no intake of food but free access to water. Several subgroups of 10 animals were randomly selected and orally given increasing doses of the products in single administration, after which they remained under observation for a period of 14 days with free access to water and food. Finally, the number of dead animals of each subgroup was quantified and the value of the DL50 was calculated (1–2).

DESCRIPTION OF THE FIGURE

FIG. 1 shows the analgesic effect on the hot plate test with mice in terms of time, expressed as percentage of increased response time with relation to the time (in hours) elapsed since the administration of the product. It is represented in grey for Tramadol, striped for compound (I) of example 6 and in black for example 1.

EXPERIMENTAL PART
1.1. Synthesis Examples

EXAMPLE 1

Synthesis of 3-(2-Dimethylaminomethyl-1-hydroxycyclohexyl)-phenyl 2-(4-Isobutyl-phenyl)-propionate

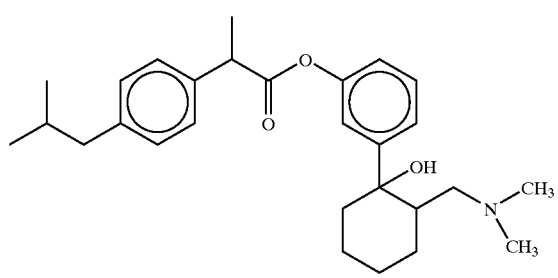

0.76 g (4.8 mmol) of carbonyldiimidazol were added to 1 g (4.8 mmol) of (±)-Ibuprofen in 60 ml of dry THF. The reaction was kept at room temperature for 2 h, after which a 60% solution of 0.59 g (2.4 mmol) of (RR,SS)-3-(2-dimethylaminomethyl-1-hydroxy-cyclohexyl)-phenol previously treated with 0.1 g (2.5 mmol) of sodium hydride in mineral oil was added.

The reaction was left at room temperature for 16 h. It was concentrated to dryness and the residue was treated with 100 ml of dichloromethane and washed with 2×50 ml of NaOH 1N and then with 100 ml of $H_2O$.

The organic phase was dried and concentrated and the residue was chromatographed on silica gel. By eluting with $CH_2Cl_2$/EtOH 98/2 to 96/4, 0.65 g (62%) of pure product was obtained as a colourless oil.

$^1$H-NMR (CDCl$_3$): 0.90 (d, 6H); 1.20–2.20 [m, 21H including 1.6 (d, 3H) and 2.05 (s, 6H)]; 2.32–2.44 (d.d, 1H); 2.47 (d, 2H); 3.92 (c, 1H); 6.78–6.86 (m, 1H); 7.12 (d, 2H); 7.18 (s.a., 1H); 7.22–7.34 (m, 4H).

EXAMPLE 2

Synthesis of 3-(2-Dimethylaminomethyl-1-hydroxyyclohexyl)-phenyl 2-(6-Methoxy-naphthalen-2-yl)-propionate

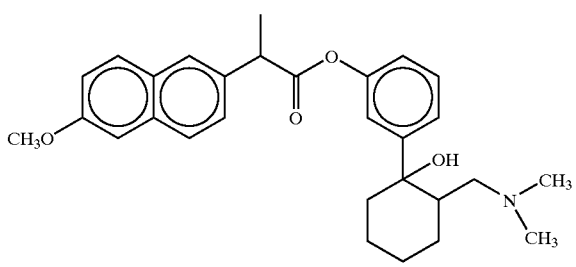

Following the process described in example 1 and substituting the (±)-Ibuprofen with (+)-6-methoxy-α-methyl-2-naphthylacetic acid (Naproxen) the title product is obtained as an oil with a 40% yield.

$^1$H-NMR (CDCl$_3$): 1.20–2.20 [m, 20 H including 1.67 (d, 3H,) and 2.06 (s, 6H]; 2.35 (dd, 1H); 3.91 (s, 3H); 4.09 (c, 1H); 6.75–6.85 (m, 1H); 7.00 (s.a., 1H); 7.15–7.35 (m, 4H); 7.50 (d.d, 1H); 7.70–7.80 (m, 3H).

EXAMPLE 3

Synthesis of 3-(2-Dimethylaminomethyl-1-hydroxycyclohexyl)-phenyl 5-Benzoyl-2,3-dihydro-1H-pyrrolizine-1-carboxylate

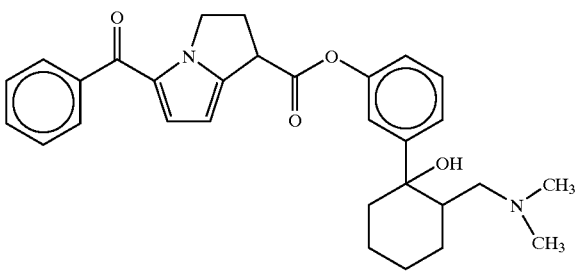

Following the process described in example 1 and substituting the (±)-Ibuprofen with (±) ketorolac (5-benzoyl-1,2-dihydro-1H-pyrrolizine-1-carboxylic acid) the title product is obtained as an oil.

$^1$H-NMR (CDCl$_3$): 1.20–2.20 (m, 17H); 2.40 (d.d, 1H); 2.80–3.10 (m, 2H); 4.28–4.72 (m, 3H); 6.26 (d, 1H); 6.87 (d, 1H); 6.90–6.98 (m, 1H); 7.30–7.60 (m, 6H); 7.78–7.88 (m, 2H)

EXAMPLE 4

Synthesis of 3-(2-Dimethylaminomethyl-cyclohex-1-enyl)-phenyl 2-(4-Isobutyl-phenyl)-propionate

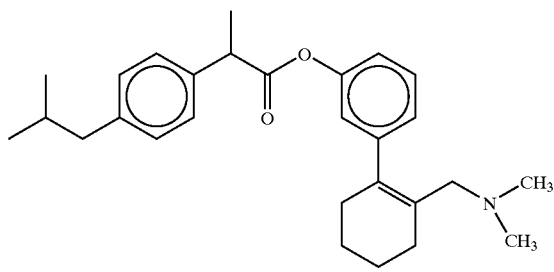

Following the process described in example 1 and substituting the (RR,SS)-3-(2-dimethylaminomethyl-1-hydroxy-cyclohexyl)-phenol with 3-(2-dimethyl-aminomethyl-1-cyclohex-1-enyl)-phenol the title product is obtained as an oil.

$^1$H-NMR (CDCl$_3$): 0.90 (d, 6H); 1.60 (d, 3H); 1.62–1.98 (m, 4H); 2.02 (s, 6H); 2.10–2.25 (m, 4H); 2.45 (d, 2H); 2.70 (s.a., 2H); 3.92 (c, 1H); 6.70 (d, 1H); 6.82–6.90 (m, 2H); 7.12 (d, 2H); 7.20–7.32 (m, 3H).

EXAMPLE 5

Synthesis of 3-(2-Dimethylaminomethyl-cyclohex-1-enyl)-phenyl 2-(6-Methoxy-naphthalen-2-yl)-propionate

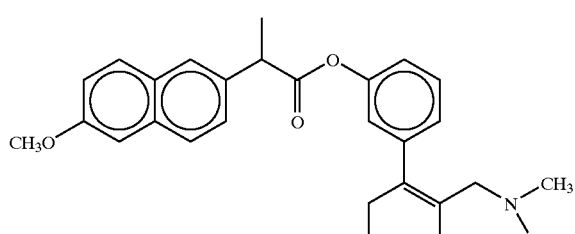

Following the process described in example 1 and substituting the (±)-Ibuprofen with (+)-6-methoxy-α-methyl-2-naphthalenacetic acid (Naproxen) and the (RR,SS)-3-(2-dimethylaminomethyl-1-hydroxy-cyclohexyl)-phenol with 3-(2-dimethylaminomethyl-cyclohex-1-enyl)-phenol the title product is obtained as an oil.

$^1$H-NMR (CDCl$_3$): 1.60–1.76 (m, 4H); 1.68 (d, 3H); 2.02 (s, 6H); 2.10–2.24 (m, 4H); 2.66 (s, 2H); 3.92 (s, 3H); 4.09 (c, 1H); 6.70 (d, 1H); 2.82–2.92 (m, 2H); 7.12–7.28 (m, 3H); 7.50 (dd, 1H); 7.70–7.78 (m, 3H).

EXAMPLE 6

3-(2-Dimethylaminomethyl-1-hydroxy-cyclohexyl)-phenyl (RR-SS)-2-hydroxybenzoate

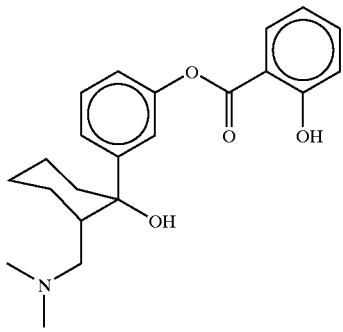

To a solution of 7.3 g (29.3 mmol) of (RR-SS)-3-(2-dimethylaminomethyl-1-hydroxycyclohexyl)-phenol and 2.6 g (32.5 mmol) of pyridine in 50 ml of $CH_2Cl_2$ a 5.8 g (29.3 mmol) solution of acetylsalicyloyl chloride in 50 ml of $CH_2Cl_2$ was added dropwise at 0° C. The mixture was kept at 0° C. for 10 h, 100 ml of methanol and 100 ml of HCl 1N were added and it was kept at 25° C. for 4 days. After evaporating the methanol and basifying to pH 8.5 with $Na_2CO_3$, it was extracted with EtOAc (3×50 ml). The combined organic extracts were dried ($MgSO_4$) and evaporated, and the residue was purified by silica gel chromatography, by eluting with $CH_9Cl_2$/MeOH/$NH_4OH$ 1000:30:3, to obtain 1.7 g (16%) of the title compound as a yellow oil.

$^1$H-NMR ($CDCl_3$): 1.20–2.25 (m, 16H) including 2.11 (s, 6H); 2.45 (dd, 1H); 6.90–7.15 (m, 3H); 7.30–7.48 (m, 3H); 7.48–7.62 (m, 1H); 8.08 (dd, 1H); 10.55 (s, 1H, exchange with $D_2O$)

EXAMPLE 7

3-(2-Dimethylaminomethyl-cyclohex-1-enyl)-phenyl 2-Hydroxybenzoate

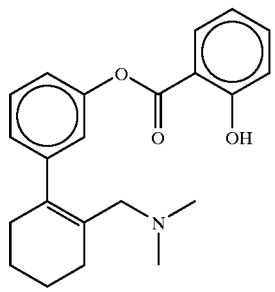

Starting from 3-(2-dimethylaminomethyl-cyclohex-1-enyl)-phenol and following the process described in example 6, the title compound was obtained as a yellow oil.

$^1$H-NMR ($CDCl_3$): 1.60–1.80 (m, 4H); 2.10 (s, 6H); 2.15–2.35 (m, 4H); 2.75 (s, 2H); 6.90–7.10 (m, 5H); 7.40 (t, 1H); 7.55 (t, 1H); 8.10 (d, 1H); 10.50 (sa, 1H, exchange with $D_2O$).

EXAMPLE 8

3-(2-Dimethylaminomethyl-1-hydroxy-cyclohexyl)-phenyl (RR-SS)-2-dimethylcarbamoyloxy-benzoate

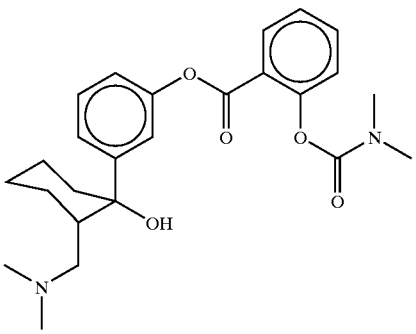

A solution of 1.82 g (8.0 nmol) of 2-dimethylcarbamoyloxybenzoyl chloride in 25 ml of $CH_2Cl_2$ was added dropwise at 0° C. to a solution of 1.9 g (7.7 nmol) of (RR-SS)-3-(2-dimethylaminomethyl-1-hydroxycyclohexyl)-phenol and 0.73 g (9.2 nmol) of pyridine in 50 ml of $CH_2Cl_2$. The mixture was maintained at 0° for 10 h, and poured over frozen water, the phases were separated and the aqueous phase was extracted with 100 ml of $CH_2Cl_2$. The organic phase was dried ($MgSO_4$) and evaporated. The residue was chromatographed on silica gel by eluting with $CH_2Cl_2$/acetone 80:20. 570 mg (48%) of the title compound was obtained as an orange oil.

$^1$H-NMR ($CDCl_3$): 1.30–1.90 (m, 9H); 2.05 (m, 1H); 2.10 (s, 6H); 2.45 (dd, 1H); 2.95 (s, 3H); 3.05 (s, 3H); 7.00–7.10 (m, 1H); 7.20 (d, 1H); 7.30–7.40 (m, 4H); 7.60 (t, 1H); 8.15 (d, 1H).

EXAMPLE 9

3-(2-Dimethylaminomethyl-cyclohex-1-enyl)-phenyl 2-Dimethylcarbamoyloxy-benzoate

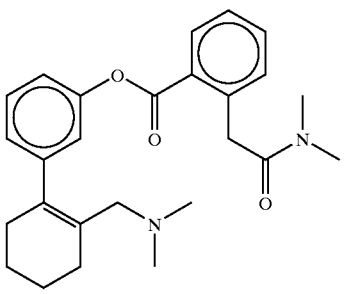

Starting from 925 mg (4.0 mmol) of 3-(2-dimethylaminomethyl-cyclohex-1-enyl)-phenol and following the process described in example 8, 190 mg (32%) of the title compound was obtained as a yellow oil.

$^1$H-NMR ($CDCl_3$): 1.70 (m, 4H); 2.07 (s, 6H); 2.10–2.30 (m, 4H); 2.75 (s, 2H); 2.95 (s, 3H); 3.10 (s, 2H); 6.90 (s, 1H); 6.95 (d, 1H); 7.05 (d, 1H); 7.20 (d, 1H); 7.30–7.45 (m, 2H); 7.65 (t, 1H); 8.20 (d, 1H)

Examples of Pharmacological Results

Table 1 below shows the results of the pharmacological activity of several examples of the invention product, as well as Tramadol. The results are expressed as percentage of increased response time on the hot plate test.

Table 2 shows the acute toxicity figures of Tramadol and of examples of the invention product, where the lower toxicity of the latter can be observed.

Analgesic Activity in Mice of the Products on the Hot Plate

TABLE 1

| PRODUCT (15 mg/kg, intraperitoneal adm.) | % response time increase (n = 20) |
| --- | --- |
| Tramadol | 218 ± 98 |
| EXAMPLE 1 | 568 ± 100 |
| EXAMPLE 2 | 539 ± 50 |
| EXAMPLE 3 | 416 ± 146 |
| EXAMPLE 4 | 333 ± 134 |
| EXAMPLE 5 | 356 ± 151 |
| EXAMPLE 6 | 546 ± 63 |
| EXAMPLE 7 | 634 ± 42 |
| EXAMPLE 8 | 327 ± 65 |
| EXAMPLE 9 | 465 ± 13 |

TABLE 2

| PRODUCT (20 µmol/kg, oral adm.) | % response time increase on hot plate (n = 20–40) | DL50 approx. (mg/kg) Oral adm. |
| --- | --- | --- |
| TRAMADOL | 87 ± 23 | 350 |
| EXAMPLE 6 | 248 ± 72 | 550 |
| EXAMPLE 1 | 210 ± 88 | 900 |

What is claimed is:

1. A Compound of formula (I):

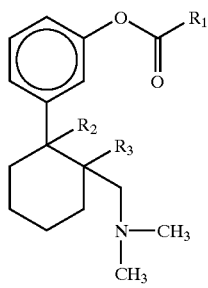
(I)

where $R_1$ is:

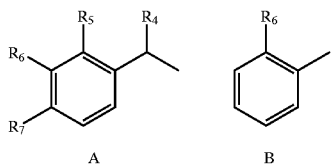

$R_2$ is: OH;
$R_3$ is: H;
or $R_2$ and $R_3$ together form a double bond;
$R_4$ is: H or $C_1$–$C_2$ alkyl;
$R_5$ is: H, $NH_2$, NH—$R_{11}$ or O—$R_{11}$;
$R_6$ is: H, CO—$R_{11}$, O—$R_{11}$ or halogen;
$R_7$ is: H, $C_1$–$C_5$ alkyl, $C_2$–$C_5$ O-alkenyl, phenyl, or $R_6$ and $R_7$ are —CH=$CR_{12}$—$CR_{13}$=CH—, forming an unsubstituted or substituted with $R_{12}$ or $R_{13}$ condensed aromatic ring;

$R_8$ is: OH, —O—CO—N($CH_3$)$_2$ or NH—$R_{11}$;
$R_{11}$ is: phenyl; phenyl unsubstituted or substituted by 1 or more of the following substituents: halogen (Cl, Br, I), $NO_2$, $C_1$–$C_6$ alkyl, $C_2$–$C_6$ alkenyl, OH, or $NH_2$;
$R_{12}$ and $R_{13}$ are: H, or $C_1$–$C_3$ O-alkyl, whether equal or different; its salts and optical isomers.

2. Compound as claimed in claim 1, wherein $R_1$ is A, and $R_4$ is methyl or H, $R_5$ is $NH_2$, 2,5-dichlorophenylamino, or H, $R_6$ is substituted CO-phenyl or H, $R_7$ is isobutyl or H, or $R_6$ and $R_7$ form a substituted condensed aromatic ring.

3. Compound as claimed in claim 1, wherein $R_1$ is B, and $R_8$ is OH or —O—CO—N($CH_3$)$_2$.

4. Compound as claimed in claim 1, wherein $R_1$, is C, and $R_9$ is methyl or H, or forms a —$CH_2$—$CH_2$— group with $R_{10}$, and $R_{11}$ is phenyl or tolyl.

5. Compound as claimed in claim 2, wherein it is selected form one of the following:

3-(2-dimethylaminomethyl-1-hydroxy-cyclohexyl)-phenyl 2-(4-isobutyl-phenyl)-propionate;

3-(2-dimethylaminomethyl-1-hydroxy-cyclohexyl)-phenyl 2-(6-methoxy-naphthalen-2-yl)-propionate;

3-(2-dimethylaminomethyl-cyclohexyl-1-enyl)-phenyl 2-(4-isobutyl-phenyl)-propionate;

3-(2-dimethylaminomethyl-cyclohexyl-1-enyl)-phenyl 2-(6-methoxy-naphthalen-2-yl)-propionate.

6. Compound as claimed in claim 3, wherein it is selected form one of the following:

3-(2-dimethylaminomethyl-1-hydroxy-cyclohexyl)-phenyl 2-hydroxybenzoate;

3-(2-dimethylaminomethyl-cyclohexyl-1-enyl)-phenyl 2-hydroxybenzoate;

3-(2-dimethylaminomethyl-1-hydroxy-cyclohexyl)-phenyl 2-dimethylcarbamoyloxy-benzoate;

3-(2-dimethylaminomethyl-cyclohexyl-1-enyl)-phenyl 2-dimethylcarbamoyloxy-benzoate.

7. Process for obtaining a compound as claimed in claim 1, wherein in that a compound of formula (II) is reacted with a compound of formula (III):

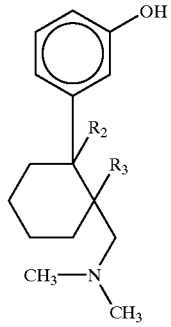
II

III where:

$R_2$ is: OH;
$R_3$ is: OH;
or $R_2$ and $R_3$ together form a double bond;
X=OH, Halogen,

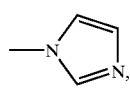

O—$R_{14}$ or —CO—$R_{15}$, $R_{14}$=$C_{1-6}$ alkyl, phenyl, and $R_{15}$=alkyl, a phenyl ring or a heteroyclic ring;

$R_1$=

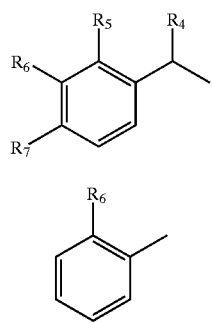

$R_4$ is: H or $C_1$-$C_2$ alkyl;

$R_5$ is: H, $NH_2$, NH—$R_{11}$ or O—$R_{11}$;

$R_6$ is: H, CO—$R_{11}$, O—$R_{11}$ or halogen;

$R_7$ is: H, $C_1$-$C_5$ alkyl, $C_2$-$C_5$ O-alkenyl, phenyl, or $R_6$ and $R_7$ are —CH=$CR_{12}$—$CR_{13}$=CH—, forming an unsubstituted or substituted with $R_{12}$ or $R_{13}$ condensed aromatic ring;

$R_4$ is: OH, —O—CO—N $(CH_3)_2$ or NH—$R_{11}$;

$R_9$ and $R_{10}$ are: H or $C_1$-$C_4$ alkyl, whether equal or different, or form a —$CH_2$—$CH_2$— group;

$R_{11}$ is: phenyl, phenyl, unsubstituted or substituted with by 1 or more of the following substituents: halogen (Cl, Br, I), $NO_2$, $C_1$-$C_6$ alkyl, $C_2$-$C_6$ alkenyl, OH, or $NH_2$;

$R_{12}$ and $R_{13}$ are: H or $C_1$-$C_3$ O-alkyl, whether equal or different;

in an inert solvent, in a temperature range of −20° to 120° C., in the presence or absence of a condensation promoting agent.

8. The process as claimed in claim 7, wherein said inert solvent is dichloromethane or tetrahydrofuran.

9. The process as claimed in claim 7, wherein said condensation promoting agent is carbonyldiimidazol or dicyclohexylcarbo-diimida.

10. The process as claimed in claim 7, wherein said temperature range is from 0° to 35° C.

11. A method for treatment of pain according to claim 1, further comprising the step of:

administering orally to a human being in need of said treatment for pain an effective dose of a compound of formula (I).

* * * * *

UNITED STATES PATENT AND TRADEMARK OFFICE
CERTIFICATE OF CORRECTION

PATENT NO.    : 6,455,585 B1
DATED         : September 24, 2002
INVENTOR(S)   : Juan Carlos Del Castillo Nieto et al.

It is certified that error appears in the above-identified patent and that said Letters Patent is hereby corrected as shown below:

<u>Title page, Item [54] and Column 1, lines 1 and 2,</u>
Title, should read -- ESTERS DERIVED FROM SUBSTITUTED PHENYL-CYCLOHEXYL COMPOUNDS --.

Signed and Sealed this

Sixth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,455,585 B1
DATED : September 24, 2002
INVENTOR(S) : Juan Carlos Del Castillo Nisto et al.

It is certified that error appears in the above-identified patent and that said Letters Patent is hereby corrected as shown below:

Title page, Item [54] and Column 1, lines 1 and 2,
Title, should read -- ESTERS DERIVED FROM SUBSTITUTED PHENYL-CYCLOHEXYL COMPOUNDS --.

Column 8,
Line 42, Example 9 should read:
-- 3-(2-dimethylaminomethyl-cyclohex-1-enyl)-phenyl dimethylcarbamoyloxy-benzoate

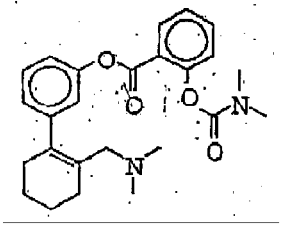

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO.   : 6,455,585 B1
DATED        : September 24, 2002
INVENTOR(S)  : Juan Carlos Del Castillo Nisto et al.

It is certified that error appears in the above-identified patent and that said Letters Patent is hereby corrected as shown below:

Column 11,
Line 50, "$R_6$" in compound "B" should set forth as "$R_8$";

Column 13,
Line 20, "$R_6$" in compound "B" should set forth as "$R_8$"; and

Column 14,
Line 5, "$R_9$" should be set forth as "$R_8$".

Signed and Sealed this

Fourth Day of January, 2005

JON W. DUDAS
*Director of the United States Patent and Trademark Office*